United States Patent [19]

Lawlis, Jr. et al.

[11] Patent Number: 5,378,621

[45] Date of Patent: Jan. 3, 1995

[54] KILLING CELLS WITHOUT LYSIS IN A METHOD FOR ENZYME RECOVERY FROM A FERMENTATION BROTH

[75] Inventors: Virgil B. Lawlis, Jr., San Mateo; Henry G. Heinsohn, Pacifica; Enrique F. Baliu, San Bruno, all of Calif.

[73] Assignee: Genencor, Inc., San Francisco, Calif.

[21] Appl. No.: 57,851

[22] Filed: May 7, 1993

Related U.S. Application Data

[63] Continuation of Ser. No. 799,864, Nov. 27, 1991, abandoned, which is a continuation of Ser. No. 365,945, Jun. 13, 1989, abandoned.

[51] Int. Cl.$^6$ .............. C12N 9/00; C12P 21/00
[52] U.S. Cl. ................... 435/183; 435/171; 435/71.1; 435/814; 435/911; 435/917; 435/942; 435/256.8; 435/254.1; 530/412; 530/823; 530/824
[58] Field of Search ............ 435/183, 814, 69.1, 435/71.1; 424/605, 243, 244, 252.1, 254.1, 259, 260, 261

[56] References Cited

U.S. PATENT DOCUMENTS

| | | | |
|---|---|---|---|
| 1,908,225 | 5/1933 | Currie et al. | 435/823 |
| 3,134,723 | 5/1964 | Corman | 435/823 |
| 3,345,268 | 10/1967 | Corman | 435/814 |
| 3,779,868 | 12/1973 | Nikolaev et al. | 435/823 |
| 3,816,260 | 6/1974 | Sugiyama | 436/206 |
| 3,890,198 | 6/1975 | Kobayashi et al. | 435/206 |
| 3,917,510 | 11/1975 | Kitamura et al. | 435/259 |
| 3,961,080 | 6/1976 | Sugimoto et al. | 426/60 |
| 4,299,858 | 11/1981 | Aubert et al. | 426/656 |
| 4,596,778 | 6/1986 | Hitzman | 435/252.1 |
| 4,601,986 | 7/1986 | Wegner et al. | 435/71.1 |
| 4,647,458 | 3/1987 | Ueno et al. | 424/605 |
| 4,654,306 | 3/1987 | Entani et al. | 435/823 |
| 4,725,544 | 2/1988 | Jan et al. | 435/814 |
| 4,935,360 | 6/1990 | Klemps et al. | 435/823 |
| 5,155,040 | 10/1992 | Kula et al. | 435/183 |

FOREIGN PATENT DOCUMENTS 0148709  7/1985  European Pat. Off. ......... 424/605

OTHER PUBLICATIONS

Rusul, G. et al., "Growth and Aflotoxin Production by *Aspergillus parasiticis* NRRL2999 in The Presence of Acetic or Propionic Acid and at Different Initial pH Values," *J. Food Protection*, 1987 vol. 50, No. 11, pp. 900 914 919.

Hentges D. J., "Influence of pH on the Inhibitory Activity of Formic and Acetic Acids for Shigella" *J. Bacteriology*, vol. 93, No. 6, pp. 2029-2030, 1967.

*Primary Examiner*—Marian Knode
*Attorney, Agent, or Firm*—Burns, Doane, Swecker & Mathis

[57] ABSTRACT

This invention provides a method for killing fungal cells without lysing in fermentation processes in order to prepare the fermentation mixture for processing to recover or extract an extracellularly expressed enzyme from the fermentation mixture. A preferred method of this invention comprises adjusting the pH of the fermentation mixture to less than 2.79 using a mineral acid, then adding sufficient acetic acid to the mixture to affect a substantially complete cell kill in mixture. A salt of the acetic acid can be used. The organic acid or salt can be added, then the pH adjusted to the desired level. Other organic acids can be used, in which case the pH of the mixture is adjusted to the pK$_a$ of the selected organic acid before the organic acid is added to the mixture. The method of this invention is useful for stopping the growth and killing the cells in any microorganism, culture or fermentation such as those containing yeast, bacteria or fungi and is particularly useful in systems where it is desired to kill the cells without lysing them.

4 Claims, No Drawings

KILLING CELLS WITHOUT LYSIS IN A METHOD FOR ENZYME RECOVERY FROM A FERMENTATION BROTH

This application is a continuation of application Ser. No. 07/799,864, filed Nov. 27, 1991, now abandoned, which is a continuation of application Ser. No. 07/365,945, filed Jun. 13, 1989 now abandoned.

FIELD OF THE INVENTION

This invention relates to the killing of cells in fermentation type of growth of yeast, bacterium or fungi.

BACKGROUND OF THE INVENTION

In the various processes of culturing or fermenting microorganisms, it is sometimes necessary at the conclusion of the growth of the culture or the conclusion of the fermentation process to be able to kill the active cells in the mixture so that the growth activity is stopped and the desired product can be recovered from the culture or fermentation mixture. This is particularly true when organisms containing recombinant DNA are grown as production hosts and it is necessary to prevent any viable recombinant organisms from being released into the environment.

It is sometimes desirable to also lyse the cells at the time the cells are killed in order to recover any desired product which is produced intracellularly. One conventional way that cells are killed and lysed is by the use of heat. U.S. Pat. No. 4,601,986 to Wegner, et al. is an example of the use of heat to kill the cells and stop the growth of microorganism cultures. Another method useful on certain microorganisms is to change the osmotic pressure which causes the cells to lyse. An example of this method is illustrated in U.S. Pat. No. 4,299,858 to Aubert, et al. Another conventional method used for lysing cells is by introduction of enzymes which break down the cell walls or membranes. Examples of this method are disclosed in U.S. Pat. No. 3,816,260 to Sugiyama, U.S. Pat. No. 3,890,198 to Kobayashi, et al. and U.S. Pat. No. 3,917,510 to Kitamura, et al. The disclosures of the above patents are incorporated herein by reference.

However, in other instances it is desirable to simply kill the cells to stop the microorganism activity without lysing the cells. This is particularly true in systems where the cells manufacture and secrete the desired product. In such systems it is very desirable to kill the cells without lysing the cells, because lysing the cells releases additional cell debris and materials, thus making recovery and purification of the desired secreted product more difficult and costly. Therefore, when the cells in such a system can be killed without lysing them, process efficiencies in recovery and purification of the secreted products are recognized.

In many systems the host microorganism is difficult to kill, for example fungi. Conventional methods, such as heat, are too severe and will destroy or alter the desired secreted product before the cells are killed. In such systems the product must be recovered without killing the cells, which requires the use of tedious and costly containment procedures and equipment.

In large scale commercial fermentation processes, it is desirable to have more efficient and faster methods for killing the cells and stopping the cell growth so the resulting fermentation mixture can be processed to extract and recover the desired product being produced without lysing the cells thus eliminating the need for containment. The heat method and other known methods for killing cells are too slow and energy inefficient for commercial use and often result in unwanted lysing of the cells. In addition, many of the conventional methods for killing cells are not compatible with culture and fermentation processes for microbial production of enzymes. Conventional methods frequently denature or alter the desired enzyme before it can be isolated and recovered, or those methods introduce materials, e.g., other enzymes, which make the isolation, recovery and purification of the desired enzyme product more difficult, less efficient and, consequently, more expensive.

It is, therefore, an object of this invention to provide a faster, more efficient method for killing cells. It is a further object of this invention to facilitate the extraction and product recovery processing of enzyme products found in a fermentation or culture mixture or medium. It is still a further object of this invention to provide a method for effecting desired cell kill which is compatible with microbial production of enzymes and the recovery and purification of such microbially produced enzymes.

SUMMARY OF THE INVENTION

In its broad aspect, this invention is a method for killing microorganisms in a growth, culture or fermentation medium wherein said microorganisms are selected from the group consisting of yeast, bacteria and fungi which method comprises the steps of:
(a) selecting a compatible organic acid having 1 to 5 carbon atoms or a compatible salt thereof; and then, in either order:
(b) adjusting the pH of the medium to a value equal to or less than the $pK_a$ of the selected compatible organic acid or compatible organic acid salt; and
(c) adding a sufficient amount of the selected compatible organic acid or compatible organic acid salt to effect a substantially complete kill of the microorganism in the medium.

In a preferred aspect, this invention is a method for killing cells in the growth, culture or fermentation of yeast, bacterium or fungi comprising steps (a) adjusting the pH of the growth, culture or fermentation mixture containing the yeast, bacterium or fungi to about 4.75 or less; then (b) adding sufficient acetic acid to the mixture to effect a substantially complete cell kill in the mixture.

In another aspect this invention is a composition comprising an aqueous composition comprising yeast, bacteria or fungi cells, a mineral acid in sufficient amount to lower the pH of the composition to a value equal to or less than the $pK_a$ of a preselected organic acid, and said organic acid or a salt thereof present in sufficient amount to effect substantially complete kill of the cells.

DESCRIPTION OF THE INVENTION

In the development of this invention, it has been found that the change in pH alone of a fermentation mixture does not accomplish a complete or sufficient cell kill. For example, in a fermentation of an *Aspergillus niger* for the production of chymosin, reducing the pH to about 2 using sulfuric acid does not accomplish the desired degree of cell kill. Therefore, it has been necessary in the past to heat the fermentation mixture to sufficiently kill the cells to stop the fermentation process in order to prepare the mixture for recovery of the chymosin product.

In a preferred embodiment of this invention it has been found that acetic acid is particularly useful in killing cells in fermentation processes, provided that the pH of the fermentation mixture is first adjusted to about 4.75 or below by the addition of a mineral acid such as sulfuric acid, then the acetic acid is added. It has surprisingly been found that the when this method is used the amount of acetic acid which is needed to accomplish substantially complete killing of the cells in the fermentation mixture is relatively small. In general, a complete cell kill will be obtained by this method with only about 1 to 2% by weight of acetic acid. In some culture or fermentation mixtures, it may be necessary to use higher amounts of acetic acid such as about 10% or more by weight based upon the total weight of the mixture, while in other processes a satisfactory level of cell kill may be obtained using as little as 0.25% by weight of acetic acid. In general, however, it has been found that the amount of acetic acid added after the adjustment of the pH of the mixture will be between about 0.5% to about 10% by weight, preferably between about 0.75% and 5% by weight, more preferably between about 1% and 3% by weight.

More generally, the process of this invention can be employed using any desired organic acid following the above steps, provided the pH of the culture or fermentation mixture is first adjusted using a mineral acid to a pH approximately equal to or less than the $pK_a$ of the organic acid selected for use for the cell kill. After the pH is adjusted to the proper level, the organic acid is added in an amount sufficient to effect the desired cell kill. For example, if formic acid is to be used to accomplish the cell kill, the pH of the mixture is adjusted with a mineral acid to about 3.75 or less, then formic acid is added to accomplish the cell kill. If propionic acid is selected for use, the pH will be adjusted about 4.87 or less, then the propionic acid added to the mixture. The organic acid can be any suitable and compatible acid having 1 to about 5 carbon atoms. The organic acid selected should be one which is compatible with and is not destructive of the desired product being produced in the culture or fermentation mixture and should be one which does not interfere with the separation, recovery and purification methods used to recover the desired product from the mixture.

It has also been found that it is not necessary to adjust the pH of the mixture before adding the organic acid. The organic acid can be added to the mixture, then the mineral acid added to adjust the pH to the preferred level for practice of this invention. As mentioned below, the same is true for use of the salt of the organic acid. The salt may be added, then the pH adjusted. In its broad aspect, it is merely important in the practice of this invention to have the organic acid or salt thereof in the mixture which has a pH at or below the $pK_a$ value of the organic acid selected for use.

While not limited to or necessarily based on the following theory, it is believed that this invention achieves the unexpectedly efficient and complete cell kill by the following mechanism. By reducing the pH of the mixture or media to a value equal to or less than the $pK_a$ of the organic acid to be used, the acid is protonated or uncharged and becomes "invisible" to the cell as an acid. The cell may then take up or import the neutral acid compound in the usual manner as a nutrient, because the cell does not see the compound as an acid. Once inside the cell, the acid is recognized and then alters the pH within the cell which kills the cell. Following this theory of the mechanism, it is apparently desirable to select an organic acid that the cell will be likely to take in as a nutrient in the acid's protonated form. A preferred acid is acetic acid because it is effective with a wide range of cells and because it is one of the lowest cost acids available. Other effective acids can be used depending on the cell cultures involved and the economics of the process.

The concentration of the organic acid is not critical, but should be of a high enough concentration so that the cell mixture is not excessively diluted when the organic acid is added. When acetic acid is used, glacial acetic acid is a convenient form.

It will also be recognized by those skilled in the art that salts of the organic acids may be used as well. For example, instead of acetic acid, sodium acetate may be used to form acetic acid in situ. The acid salt, or at least a portion thereof, will become protonated in the solution where the pH has been lowered by the mineral acid to a value below the $pK_a$ of the organic acid. As will also be apparent to one skilled in the art, the pH adjustment of the solution will be different when an acid salt is used than when the acid itself is used, because the salt will not affect the pH, as will the organic acid. Any organic acid salt may be used which is compatible with the solution and the components of the solution which are to be recovered from the solution after the cell kill is effected. As mentioned above, the pH of the mixture may be adjusted to the acid $pK_a$ value or lower either before or after the organic acid or salt thereof is added to the mixture. However, as a preferred practice of this invention, the pH is first adjusted to the desired value with a mineral acid, then the organic acid is added.

The mineral acids that can be used to adjust the $pK_a$ of the mixtures according to the method of this invention include sulfuric acid, hydrochloric acid, other mineral acids capable of reducing the pH of the cell mixture to a value equal to or less than the $pK_a$ of the organic acid to be used to kill the cells in the mixture. It is desirable to select a mineral acid for adjustment of the pH which is compatible with the methods and equipment to be used to separate or extract the desired product from the fermentation or culture mixture or media. The concentration of the mineral acid used should be high enough so that the pH of the cell mixture can be adjusted to the desired level without unduly diluting the mixture.

Having described in general aspects of this invention, the invention is now illustrated by the specific embodiments described in the following examples.

EXAMPLES

In the following examples, the samples were obtained from the fermentation of an *aspergillus niger* var. awamori typically run with 6% or 10% soy meal/glucose and harvested after 4 to 5 days. For purposes of testing the cell kill provided by this invention, particular cell production techniques are not important. The following comparative results illustrate various embodiments of this invention using a standard serial dilution test to determine the quantity of living cells remaining after the cell kill is effected. After the cell kill treatment, the samples were brought to pH 5.5, were serially diluted in 0.85% NaCl, spread plated on CMA plates, incubated at 37 degrees Celsius for 72 hours and reported in CFU/ml.

EXAMPLE I

This example illustrates the effectiveness of the method of this invention in producing essentially complete cell kill of *A. niger* var. awamori.

Two samples of an *A. niger* var. awamori fermentation mixture were adjusted to pH 2.0 with sulfuric acid. After the acid was well mixed, 4% by volume of glacial acetic acid was added to one sample. Both samples were stored overnight in a cold room then tested for cell kill. The serial dilution test results were as follows:

| Sample | Acetic Acid | $10^9$ | $10^8$ | $10^7$ | $10^6$ | $10^5$ | $10^4$ | $10^3$ | $10^2$ | 10 |
|---|---|---|---|---|---|---|---|---|---|---|
| A | 0 | 0 | 0 | 0 | 0 | 0 | 0 | 3 | 72 | TNTC |
| B | 4% (vol) | 0 | 0 | 0 | 0 | 0 | 0 | 0 | 0 | |

(TNTC means the cell growth cultures were too numerous to count.)

This example shows that the sulfuric acid alone did not effect a complete cell kill, whereas the combination of the sulfuric acid and acetic acid did effect a complete cell kill.

Example II

In this example a portion of a fermentation mixture similar to that of Example I was cooled to 12° C. and held for 60 hours. Three examples were taken from the mixture: one was untreated and one was treated with $H_2SO_4$ alone to pH 2.0. The third sample was treated with $H_2SO_4$ to a pH 2.0, glacial acetic acid was added in the amount of 1% of the weight of the mixture sample then the mixture was aerated and agitated for approximately one hour. All three samples were adjusted to pH 5.5, with NaOH, serially diluted, plated and incubated for five days at 37° C. The test results were as follows:

| Sample | $10^{-4}$ | $10^{-3}$ | $10^{-2}$ | .1 ml | 1 ml |
|---|---|---|---|---|---|
| No treatment | 30 | TNTC | TNTC | TNTC | TNTC |
| $H_2SO_4$ only (pH 2.0) | 0 | 0 | 0 | 2 | 19 |
| $H_2SO_4$ (pH 2.0)/1% acetic acid | 0 | 0 | 0 | 0 | 0 |

This example indicates that the acetic acid/sulfuric acid treatment provides at least 6 log reduction in cells.

Example III

In this example a fermentation broth similar to that of Example I was used to show the affect of the pH adjustment on the cell kill. Also, in this example the organic acid salt is used instead of the organic acid. In the following, samples 1–5 were used as is and 6–10 had 2% acetate (as 4.53 g of sodium acetate per 100 ml) added before pH adjustment. The pH of samples 1–5 before adjustment was about 5.8 and of samples 6–10 about 6.0. The pH of all samples was then adjusted to the values shown below, except for sample 4 which was not adjusted and which served as control sample of the broth. The pH was adjusted in each sample with $H_2SO_4$ or $NH_4OH$ to obtain the pH indicated.

| Sample | pH After Adjustment |
|---|---|
| 1 | 2.5 |
| 2 | 3.74 |
| 3 | 4.70 |
| 4 | 5.86 (no adjustment) |
| 5 | 6.7 |
| 6 | 2.79 |
| 7 | 3.76 |
| 8 | 4.76 |
| 9 | 5.6 |
| 10 | 6.8 |

All samples were stored on ice for 4 hours then the pH adjusted to 5.5 for plating on CMA plates with antibiotics. The plates were incubated at SPC for 7 days. The test results were as follows:

| Sample | $10^5$ | $10^4$ | $10^3$ | $10^2$ | 0.1 ml | 1 ml |
|---|---|---|---|---|---|---|
| 1 | 0 | 2 | 7 | 55 | TNTC | TNTC |
| 2 | 0 | 5 | 128 | TNTC | TNTC | TNTC |
| 3 | 1 | 47 | TNTC | TNTC | TNTC | TNTC |
| 4 | 3 | 64 | TNTC | TNTC | TNTC | TNTC |
| 5 | 3 | 66 | TNTC | TNTC | TNTC | TNTC |
| 6 | 0 | 0 | 0 | 0 | 2 | 62 |
| 7 | 0 | 1 | 2 | 37 | TNTC | TNTC |
| 8 | 0 | 1 | 3 | 56 | TNTC | TNTC |
| 9 | 3 | 35 | TNTC | TNTC | TNTC | TNTC |
| 10 | 3 | 34 | TNTC | TNTC | TNTC | TNTC |

This example illustrates the importance of adjusting the pH of the mixture to a value at or preferably below the $pK_a$ of the organic acid used. A more complete cell kill would be obtained at the lower pH ranges if higher amounts of acetate were used, such as 4%. However, the lower level of acetate was used in this example so the effect of the pH could be seen.

Example IV

This example illustrates the use of the present invention to kill yeast cells. For this example a yeast known as *Saccharomyces cerevisiae* was grown on a standard "YM" medium, available from Difco, at 250 rpm for 24 hrs at 37° C. As in Example 3 above, 10 samples were taken, samples 6–10 treated with 2% acetate (as sodium acetate), the pH adjusted to the value shown below, then plated and incubated for 4 hours.

| Sample | pH After Adjustment |
|---|---|
| 1 | 2.55 |
| 2 | 3.63 |
| 3 | 4.40 |
| 4 | 5.78 |
| 5 | 6.84 |
| 6 | 2.8 |
| 7 | 3.6 |
| 8 | 4.72 |
| 9 | 5.68 |
| 10 | 6.75 |

Test results

| Sample | $10^{-5}$ | $10^{-6}$ | $10^{-7}$ | $10^{-8}$ | -CFU/ml ($\times 10^7$) |
|---|---|---|---|---|---|
| 1 | TNTC | 42/41 | 7/2 | 1/3 | 4.2 |
| 2 | TNTC | 50/45 | 4/5 | 0/0 | 4.7 |
| 3 | TNTC | 49/48 | 3/5 | 2/1 | 4.9 |
| 4 | TNTC | 50/64 | 12/5 | 1/0 | 5.7 |
| 5 | TNTC | 43/54 | 5/9 | 1/1 | 4.9 |
| 6 | TNTC | 43/24 | 4/7 | 0/0 | 3.4 |
| 7 | TNTC | 32/34 | 5/8 | 1/1 | 3.3 |
| 8 | TNTC | 51/48 | 6/7 | 0/0 | 5.1 |
| 9 | TNTC | 56/58 | 4/5 | 1/2 | 5.7 |
| 10 | TNTC | 56/45 | 3/5 | 1/0 | 5.1 |

As can be concluded from the above, about 20% kill was obtained at pH 2.8, about 30% at pH 3.6, and no significant kill at pH 4.7, 5.7 or 6.75. While this example was run to determine the affect of pH on the effectiveness of the kill, it is apparent that a more effective kill would be achieved at higher levels of acetate, e.g., 4%. Also, as will be appreciated, it is more difficult to accurately quantify cell kill and culture growths of yeast than fungi, but this example demonstrates the usefulness of the present invention for yeast.

Having described this invention and illustrated particular embodiments of the invention, the scope of this invention is now defined by the claims that follow.

What is claimed is:

1. In a method for recovering an extracellularly produced enzyme from a fungus in a fermentation medium, wherein the improvement comprises killing the fungal cells, without lysing, by a method comprising the following steps in either order:
   (a) adjusting the pH of the medium to a value equal to or less than 2.79 with a mineral acid;
   (b) adding from about 0.25 to about 10% by weight of acetic acid or a salt thereof to the medium
to thereby kill the cells in the medium under conditions which are compatible with the extracellularly produced enzyme.

2. In a method for recovering an extracellulary produced enzyme from *Aspergillus niger* in a fermentation medium, wherein the improvement comprises killing the *Aspergillus niger* cells, without lysing, by a method comprising the following steps in either order:
   (a) adjusting the pH of the medium to a value equal to or less than 2.79 with a mineral acid;
   (b) adding from about 0.25 to about 10% by weight of acetic acid or a salt thereof to the medium
to thereby kill the cells in the medium under conditions which are compatible with the extracellularly produced enzyme.

3. In a method for recovering an extracellularly produced enzyme from *Saccharomyces cerevisiae* in a fermentation medium, wherein the improvement comprises killing the *Saccharomyces cerevisiae* cells, without lysing, by a method comprising the following steps in either order:
   (a) adjusting the pH of the medium to a value equal to or less than 2.79 with a mineral acid;
   (b) adding from about 0.25 to about 10% by weight of acetic acid or a salt thereof to the medium
to thereby kill the cells in the medium under conditions which are compatible with the extracellularly produced enzyme.

4. The method according to claims 1, 2, or 3 wherein the mineral acid is sulfuric acid or hydrochloric acid.

* * * * *